(12) United States Patent
Rijken et al.

(10) Patent No.: US 11,413,009 B2
(45) Date of Patent: Aug. 16, 2022

(54) ADJUSTABLE ARM FOR A PATIENT MONITORING DEVICE

(71) Applicant: KONINKLIJKE PHILIPS N.V., Eindhoven (NL)

(72) Inventors: Antonius Maria Rijken, Eindhoven (NL); Wilhelmus Johannes Antonius Pasman, Eindhoven (NL); Marleen Van Aartrijk, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1030 days.

(21) Appl. No.: 15/567,093

(22) PCT Filed: Apr. 8, 2016

(86) PCT No.: PCT/EP2016/057712
§ 371 (c)(1),
(2) Date: Oct. 17, 2017

(87) PCT Pub. No.: WO2016/169787
PCT Pub. Date: Oct. 27, 2016

(65) Prior Publication Data
US 2018/0092624 A1 Apr. 5, 2018

(30) Foreign Application Priority Data

Apr. 21, 2015 (EP) .................................... 15164355

(51) Int. Cl.
*A61B 8/00* (2006.01)
*A61B 90/57* (2016.01)
(Continued)

(52) U.S. Cl.
CPC ............ *A61B 8/4218* (2013.01); *A61B 90/50* (2016.02); *A61B 90/57* (2016.02); *A61B 6/4258* (2013.01);
(Continued)

(58) Field of Classification Search
CPC ....... A61B 8/4218; A61B 90/50; A61B 90/57; A61B 6/4258; A61B 2090/508; A61B 2090/571; A61N 7/02
See application file for complete search history.

(56) References Cited

U.S. PATENT DOCUMENTS 5,631,973 A 5/1997 Green
5,779,209 A 7/1998 Rello
(Continued)

FOREIGN PATENT DOCUMENTS

CN 202184800 U 4/2012
CN 102839878 A 12/2012
(Continued)

*Primary Examiner* — Yi-Shan Yang
*Assistant Examiner* — Alexei Bykhovski

(57) ABSTRACT

The application describes an adjustable arm for a patient monitoring device to be placed on a surface portion of a patient's body, said arm comprising: at least first and second arm parts; abase to which the first arm part is connected and which includes mounting means for mounting it relative to a patient support platform; and holding means for receiving the patient monitoring device, to which the second arm part is connected; the arm parts, the base and the holding means being articulated by means of joints therebetween, which joints are fixable against movement when the patient monitoring device is in use; wherein the joints between the first arm part and the base and between second arm part and the holding means comprise multidirectional joints; wherein the base has a fixed portion and a tillable portion, the fixed portion comprising the mounting means and the first arm part being connected to the tillable portion, whereby when the said joints are fixed the adjustable arm can maintain the patient monitoring device in position on the patient surface portion while allowing for movement of the patient monitoring device due to respiration.

15 Claims, 3 Drawing Sheets

(51) Int. Cl.
*A61B 90/50* (2016.01)
*A61N 7/02* (2006.01)
*A61B 6/00* (2006.01)

(52) U.S. Cl.
CPC ... *A61B 2090/508* (2016.02); *A61B 2090/571* (2016.02); *A61N 7/02* (2013.01)

(56) References Cited

U.S. PATENT DOCUMENTS

| | | | |
|---|---|---|---|
| 2002/0074463 A1* | 6/2002 | Nakamura | A61B 90/50 248/127 |
| 2002/0177754 A1* | 11/2002 | Phillips | A61B 17/02 600/234 |
| 2005/0261591 A1 | 11/2005 | Boctor et al. | |
| 2007/0044336 A1 | 3/2007 | Iikubo et al. | |
| 2007/0100346 A1* | 5/2007 | Wyss | A61B 17/15 606/87 |
| 2007/0270685 A1 | 11/2007 | Kang et al. | |
| 2010/0204578 A1 | 8/2010 | Schmidt et al. | |
| 2013/0048818 A1* | 2/2013 | Von Pechmann | B25J 15/0019 248/276.1 |
| 2014/0039314 A1 | 2/2014 | Stoianovici et al. | |
| 2014/0157937 A1* | 6/2014 | Doi | F16M 11/2021 74/490.01 |
| 2014/0171782 A1 | 6/2014 | Bruder et al. | |
| 2015/0297305 A1* | 10/2015 | Wyslucha | F16C 11/10 248/274.1 |

FOREIGN PATENT DOCUMENTS

| | | | |
|---|---|---|---|
| CN | 202640348 U | 1/2013 | |
| CN | 103753526 A | 4/2014 | |
| CN | 104440865 A | 3/2015 | |
| EP | 1190680 A1 * | 3/2002 | ............ A61B 90/50 |
| WO | 2010087360 A1 | 8/2010 | |
| WO | 2013080124 A1 | 6/2013 | |
| WO | 2014096993 A1 | 6/2014 | |

\* cited by examiner

ADJUSTABLE ARM FOR A PATIENT MONITORING DEVICE

This application is the U.S. National Phase application under 35 U.S.C. § 371 of International Application No. PCT/EP2016/057712, filed on Apr. 8, 2016, which claims the benefit of EP Application Serial No. 15164355.8, filed Apr. 21, 2015. These applications are hereby incorporated by reference herein.

FIELD OF THE INVENTION

The present invention relates to an adjustable arm for a patient monitoring device.

BACKGROUND OF THE INVENTION

An example of a patient monitoring device is an ultrasonic or ultrasound probe. Such probes can be used in during minimally invasive cardiac interventions.

Medical ultrasonic probes come in a variety of different shapes and sizes for use in taking pictures of different parts of the body. The probe may be passed over the surface of the body by hand.

Ultrasound may be used during minimal invasive interventions in the heart, for example during heart valve repairs. This type of procedure is time consuming and it is important to have a stable image of the relevant part of the patient's body for a long period of time. Clinicians are used to control the probes manually.

In the alternative, during ultrasound-guided procedures a probe positioning device which holds the ultrasonic probe may be used.

The probe positioning device is a tool for the positioning of a measuring device, such as an ultrasound probe, in a fixed, predetermined place relative to the patient. The operation of these systems varies from completely manual, to completely automated.

In an automated probe positioning system, a control system corrects for the movement of the patient or disturbances in the environment. These systems can use a tilt, pressure or other sensor carried by the probe to collect positional data. The positioner, such as a robotic arm is coupled to the probe. The positioner can provide roll and pitch control as well as translating the probe in lateral and longitudinal directions. A processor receives signals from the sensors corresponding to the actual orientation of the probe and controls the positioner to adjust the orientation of the probe until the desired position is achieved.

The current methods, whether fully manual or fully automated, are costly, take up valuable space around the patient, and in some circumstances may still lead to difficulties in providing a stable image.

There is therefore a need for an improved adjustable arm for a patient monitoring device.

SUMMARY OF THE INVENTION

The invention is defined by the claims.

In accordance with one aspect of the invention, there is provided an adjustable arm for a patient monitoring device to be placed on a surface portion of a patient's body, said arm comprising: at least first and second arm parts; a base to which the first arm part is connected and which includes mounting means for mounting it relative to a patient support platform; and holding means for receiving the patient monitoring device, to which the second arm part is connected; the arm parts, the base and the holding means being articulated by means of joints therebetween, which joints are fixable against movement when the patient monitoring device is in use; wherein the joints between the first arm part and the base and between second arm part and the holding means comprise multidirectional joints; wherein the base has a fixed portion and a tiltable portion, the fixed portion comprising the mounting means and the first arm part being connected to the tiltable portion, whereby when the said joints are fixed the adjustable arm can maintain the patient monitoring device in position on the patient surface portion while allowing for movement of the patient monitoring device due to respiration.

The invention thus has an advantage that the principal movement of the patient is compensated for while the patient monitoring device stays at the same location on the patient's chest during the medical intervention or procedure. The positioning of the monitoring device is easy due to the plural arm parts and articulating joints.

The patient monitoring device, for example an ultrasound probe or probes, can be held on the patient's chest in a constant position for a long period of time, without the need for clinicians to hold the device or constantly re-position it.

The invention allows for the patient monitoring device to be located in position with adjustment in six degrees of freedom. After correct location of the patient monitoring device and locking of the joints, the patient monitoring device can move with one degree of freedom (up-down, because the patient lies in his or her back), in response to chest movements.

The base of the adjustable arm may include resilient means which act on the tiltable portion to urge the holding means either towards or away from the patient surface portion. The resilient means may comprise a tension or compression spring mounted on a threaded rod, the spring force being adjusted by means of a nut threaded onto the rod.

The tiltable portion of base can be releasably locked to the fixed portion by a locking pin, which pin is released after an initial fixing of the position of the patient monitoring device on the patient surface portion.

The fixed portion of the base may be formed of two parts pivotally connected together, and movable relative to one another from a closed, fixed position to an open position. By this arrangement a simple and quick release of the monitoring device and the arm away from the patient's chest is made possible, which might be vital in the event of an emergency, without any loss of the correct position of the monitoring device. Thus, the device can be repositioned at the same spot on the patient's chest for continuation of the intervention simply by pivoting the arm back to its original position. The two parts of the fixed portion of the base can be releasably locked together by a locking pin.

The joint between the first and second arm parts can be a pivotal connection and may comprise an electromotor for locking the pivotal connection. The electromotor may be controllable by a remote switch, which switch can be integrated in a foot pedal.

Another aspect of the invention provides an assembly comprising the adjustable arm as set out above and a patient monitoring device, preferably an ultrasound probe.

BRIEF DESCRIPTION OF THE DRAWINGS

Examples of the invention will now be described in detail with reference to the accompanying drawings, in which.

DETAILED DESCRIPTION OF THE EMBODIMENTS

Figure 1:
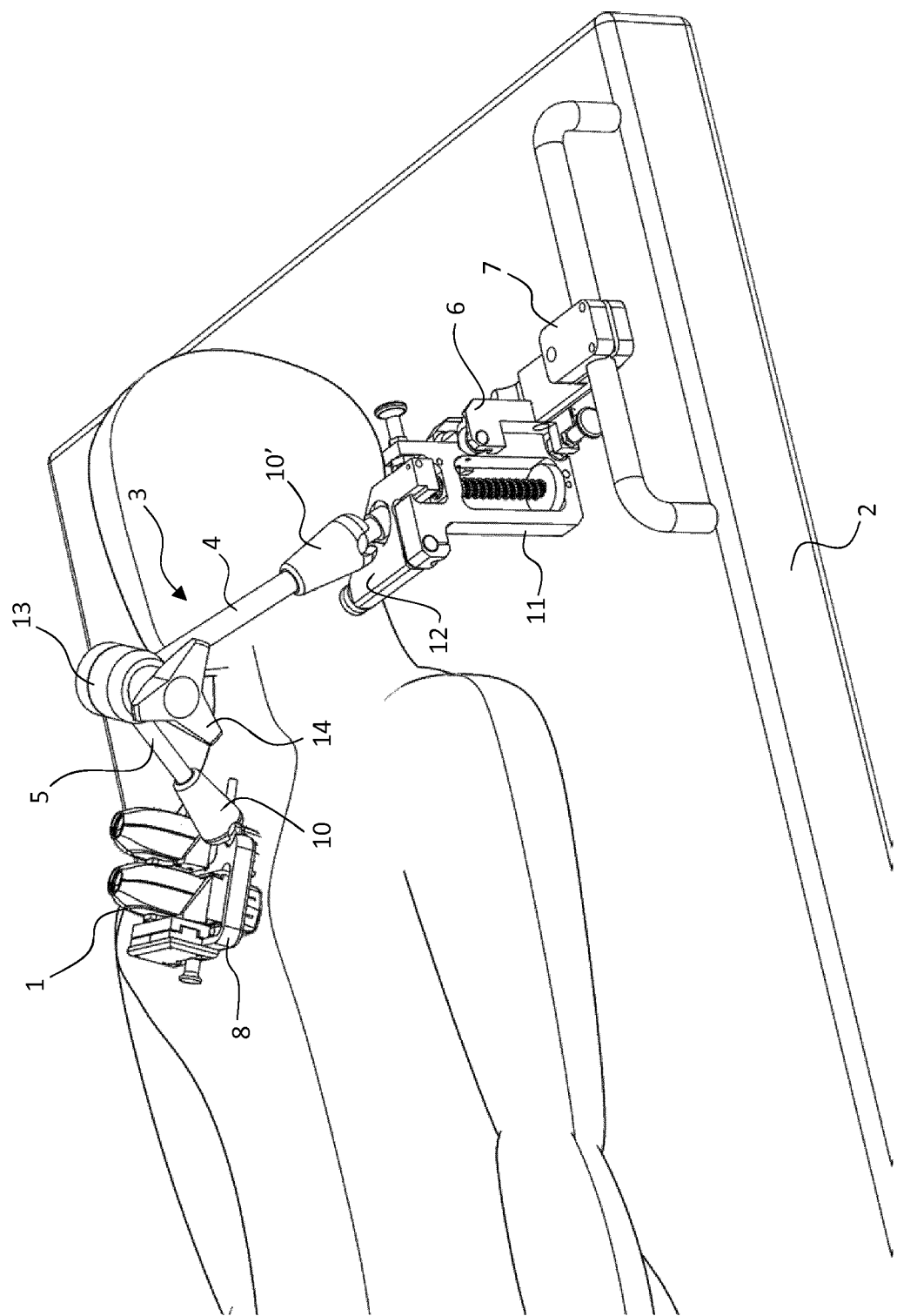
FIG. 1 is a perspective view of an adjustable arm for a patient monitoring device, this view also showing the patient lying on a patient support platform.

FIG. 1 shows one embodiment of the invention in its in use position, with a patient monitoring device 1 resting on the chest of a patient (shown schematically). The patient is lying on a patient support platform 2.

The adjustable arm 3 for the patient monitoring device comprises a first arm part 4 and a second arm part 5. The arm 3 includes a base 6 to which the first arm part 4 is connected and which includes mounting means 7 for fixing it relative to the patient support platform 2.

The arm 3 also includes a holding means 8 for holding the patient monitoring device 1. The second arm part 5 is connected to the holding means 8. The holding means in this embodiment is a bracket into which the patient monitoring device is fitted by resilient clips, but other fitting mechanisms are equally possible such as screws or bolts.

A fixable or lockable multidirectional joint 10, 10' is provided between the base 6 and the first arm part 4 and between the holding means 8 and the second arm part 5.

The base 6 has a fixed portion 11 and a tiltable portion 12. The first arm part 4 is connected to the tiltable portion 12. Thus the arm can move, even after the multidirectional joints are fixed in position, to allow for the movement of the patient monitoring device on the patient surface portion due to respiration.

The first and second arm parts 4, 5 are articulated together at a joint 13. This joint may be a simple pivot joint, or could be a multidirectional joint. The joint 13 may include a multi-pointed "star-grip" handle 14, threadedly engaged with the joint. In the illustrated embodiment the handle 14 has three points. The handle 14 may be turned manually to lock the joint, by means of a screw-thread arrangement forcing bearing surface of the joint 13 against each other.

Alternatively, joint 13 may comprise an electromotor for locking the joint, in a known fashion, using a spur gear wheel and belt arrangement. The electromotor can be controllable by a remote switch. The remote switch can be integrated in a foot pedal (not shown).

The multidirectional joints 10, 10' are preferably ball joints, formed in a conventional fashion by a male spherical part being located in a female socket with a part-spherical cavity. Such a joint allows for a full range of movements of the male and female parts relative to one another, and thus of those elements connected to the male and female parts.

In the preferred embodiment, the locking of the handle 14 automatically locks the multidirectional joints. Thus, the turning of the handle, either manually or by means of the electromotor, automatically applies a force on the male or female parts of the ball joints, along the axis of the arm parts, so as to fix them relatively to one another. For example, the male parts may be drawn towards the joint 13 by an internal cable or the tapered female parts moved away from the joint (by a longitudinal or rotational movement).

The arms parts 4, 5 and joints 10, 10' and 13 may be a proprietary item, obtained for example from Baitella AG of Zurich, under the trade name "Fisso".

In the alternative, the multidirectional joints can be locked for example by the female socket having an adjustable diameter for locking the male ball part. The socket may comprise opposing threaded socket portions through which a screw extends for adjusting the diameter, or a ring may be screwed onto a tapered socket to force the opposing socket portion together. Other conventional means of forming lockable universal joints, for example ball joints, will be well known to the person skilled in the art. The multidirectional joints could even be fixed by their own internal friction, that is by being sufficiently stiff to resist movement other than by a significant manual force.

The holding means 8 for the monitoring device 1 can be formed in any suitable fashion for mounting thereon the patient monitoring device. The male part of the multidirectional joint 10 is fitted in an aperture in the holding means 8. The patient monitoring device is in this embodiment an ultrasound probe or transducer, which operates by being placed directly against the skin of the patient.

Figure 2:
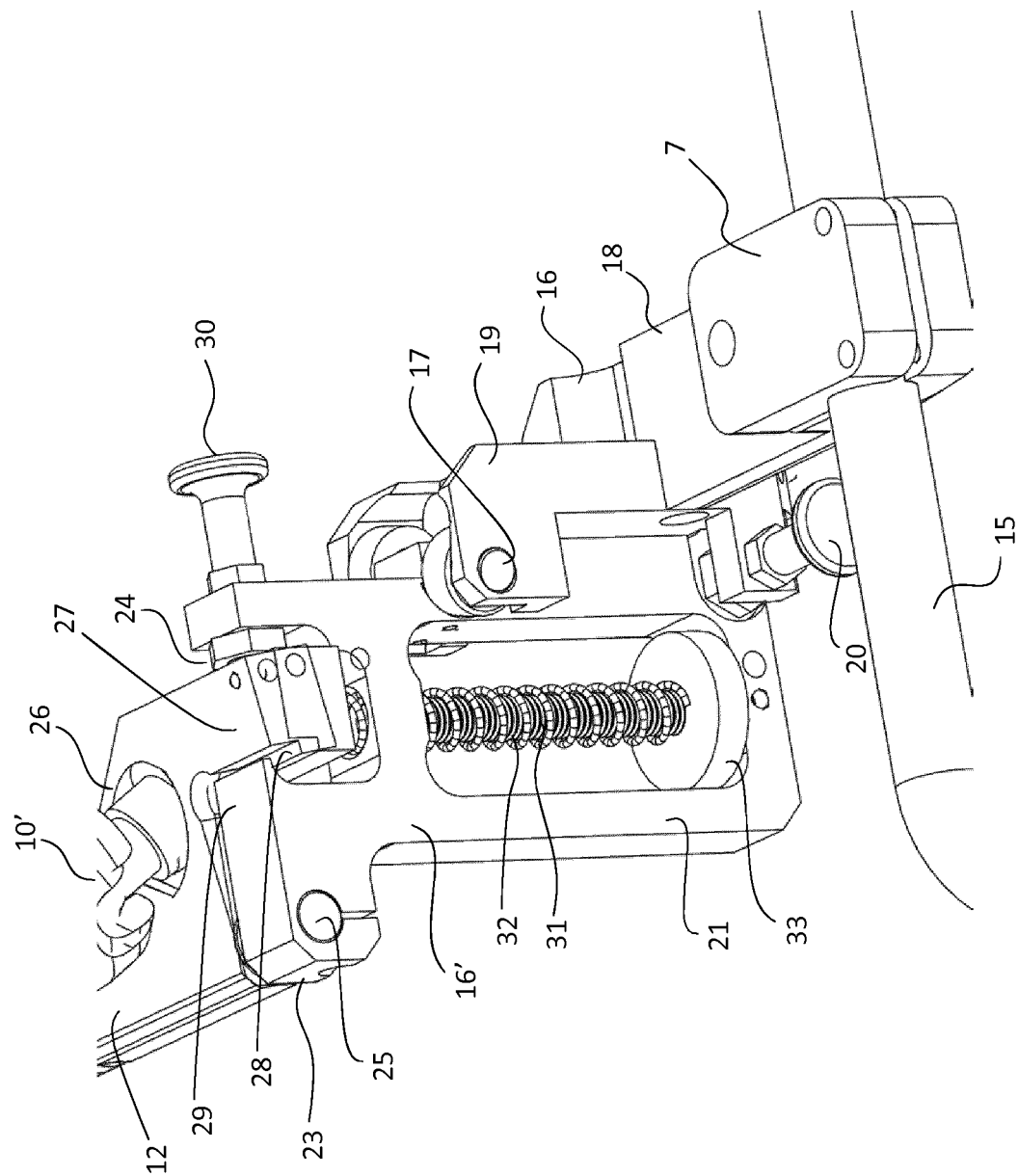
FIG. 2 is a close-up perspective view of the base of the adjustable arm for a patient monitoring device, showing its movement relative to the patient during monitoring.

The base 6 of the adjustable arm is shown most clearly in FIG. 2. As mentioned above, the base 6 has a fixed portion 11 and a tiltable portion 12. The mounting means 7 for fixing the base relative to the patient support platform 2 comprises, in the illustrated embodiment, a clamp which can be fixed, by means of locking screws, onto a bar 15 fitted onto the patient platform 2. The mounting means could alternatively be provided by any other connection mechanism, for example the screwing or bolting of the base directly onto the patient support platform or male/female parts on the base slotting together with female/male parts on the platform.

It should be noted that in FIG. 2 two positions of the tiltable part 12 can be seen, these two positions representing the upper and lower chest positions as the patient breathes in and out.

The base 6 in this embodiment is formed of two main parts, namely lower and upper base parts 16, 16', pivotally connected to one another by pivot point 17. The first arm part 4 is connected to the upper base part 16'.

The lower base part 16 includes the clamp 7, a clamp arm 18, and an upright 19. This upright 19 is slotted so as to form an opening in which the upper base part 16' can be mounted by means of the pivot point 17. The upper base part 16' can be locked in the position seen in FIG. 2, relative to the lower base part 16, by means of a locking pin 20, mounted at the base of the upright 19, which can engage in a hole in a lower portion of the upper base part.

The upper base part 16' comprises an upright frame portion 21 having an opening 22, a nose portion 23 and a recess 24 adjacent the nose portion 23 and above the opening 22. The tiltable part 12 of the base extends laterally of the upright frame portion 21 and is pivotally connected to the frame portion at the nose portion 23. The pivotal connection is formed by a pin 25 extending through the tiltable part 12 and into the nose portion 23. The pivot axis of the tiltable part 12 thus extends transversely of the patient lying position, for example 90° to the edge of the patient platform.

The male part of the multidirectional joint 10' is mounted in a central aperture 26 in the tiltable part 12.

The tiltable part 12 includes a lug 27 which extends into the recess 24. The lug has a ledge 28 which sits below a lip 29 of the frame portion 21. The lip 29 thus limits the upward movement of the tiltable part 12 as it pivots on the frame portion. The frame portion also includes a locking pin 30, opposite to the nose portion 23, which can releasably engage the lug 27 of the tiltable part in the recess 24 to lock it in one position. The locking pin 30 can be urged by a spring into the locking position, and pulled out and turned (for example by a quarter turn) to hold it in its retracted position by means of cooperating surfaces on the pin and frame portion.

Extending vertically in the opening 22 of the upper base part 16', from the bottom of the frame portion 21, is arranged a threaded rod 31 around which is fitted a spring 32. The spring 32 can be either a tension spring or a compression spring. The spring 32 extends through a hole at the top of the frame portion 21 to abut the lower surface of the tiltable part 12 in the recess 24.

A knurled circular nut or knob 33 is threadedly engaged on the lower part of the rod 31. The knob 33 can be turned to change the length of the spring 32 and thus the force which it applies to the tiltable part 12.

Where it is desired to increase the pressure of the ultrasound probe on the patient's chest (for a good acoustic contact) the spring is a compression spring. However, where the probe is heavy, and thus the gravitational force is quite high enough to ensure a good acoustic contact, a tension spring can be used. Upon application of the pulling force of the tension spring, the force on the chest wall is made lower which is more comfortable for the patient. If a tension spring is used then its ends are connected to the knob and tiltable part.

Figure 3:
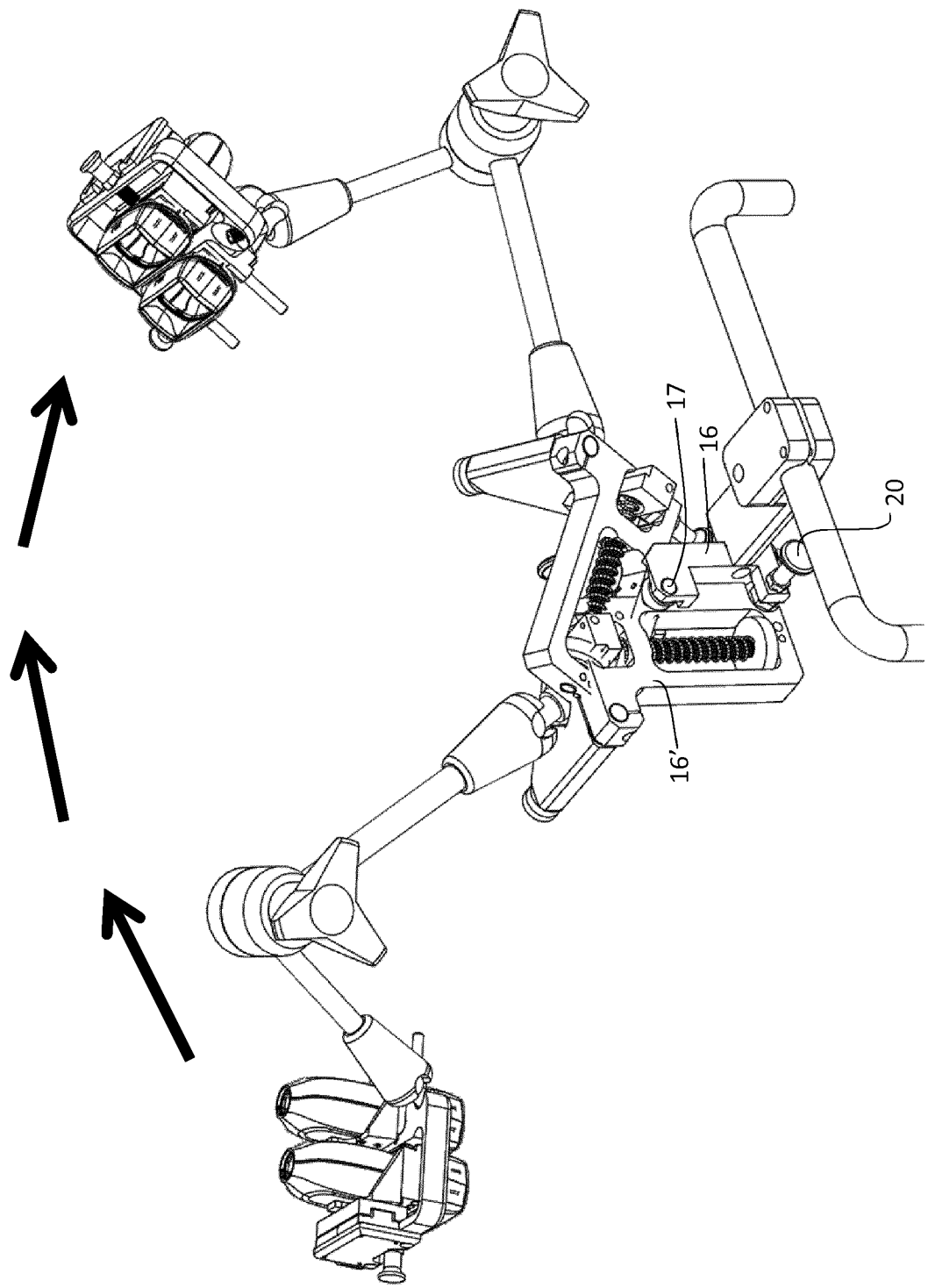
FIG. 3 is a perspective view of the adjustable arm for a patient monitoring device, showing its movement to a retracted position away from the patient.

As shown in FIG. 3, the adjustable arm 3 can be moved to retracted position, away from the head of the patient platform 2 and thus away from the patient by means of the pivot 17. The upper base part 16' is permitted to pivot relative to the lower part base part 16 by releasing the locking pin 20 from the frame portion 21. In practice the locking pin 20 is pulled from the hole in the frame portion 21 against the action of a spring.

The adjustable arm 3 of this embodiment of the invention is used as follows. The arm is clamped to the bar 15 of the patient platform 2, by means of the clamp 7, so that the clamp arm 18 extends generally horizontally inwardly of the bar 15. The frame portion 21 is generally vertical and the pivot axis of the tiltable part 12 is generally horizontal. The locking pin 30 locks the tiltable part 12 relative to the frame portion 21 in a neutral median position, that is with the ledge 28 spaced from the lip 29 of the frame portion.

The patient monitoring device 1, for example an ultrasound probe, is then fitted to the holding means 8 at the end of the adjustable arm. The upper base part 16' is pivoted away from the head of the patient platform to its refracted position, as shown in FIG. 3, by releasing the locking pin 20. The patient can then lie on the platform. After the patient is in position, the upper part 16' of the base, with the arm attached, is pivoted back into position and the locking pin 20 is slotted back into the frame portion 21.

The adjustable arm is them manoeuvred into position by hand by the attending clinician so that the ultrasound probe is resting in the correct position against the patient's chest. Through this manual manoeuvring the arm is twisted and turned at the multidirectional joints 10, 10', and the joint 13 can also turn as necessary. The patient continues to breathe normally while final adjustments are made by the clinician.

The star-grip handle 14 of the joint 13 can then be tightened either manually or by the electromotor, switched by the foot pedal, after the ultrasonic probe is positioned by the clinician moving the holding means 8 by hand, this movement being facilitated by the universal joints 10, 10'. Then the locking pin 30 is released and placed in its retracted position. This release of the locking pin 30 allows the tiltable part 12, and thus the arm parts 4, 5 connected thereto, to move with the respiration of the patient. In other words, the arm can tilt as the patient's chest rises and falls while allowing the patient monitoring device to remain at the same position on the patient.

As stated above, in FIG. 2 two positions of tiltable part 12 are illustrated, one above the other, these two positions representing the upper and lower chest positions as the patient breathes in and out.

The movement of the tiltable part 12 and thus the arm parts 4, 5 is controlled by means of the spring 32. The force with which the ultrasound probe presses on the patient's chest (for a good acoustic contact) can be set by adjusting of the spring. In the alternative, the spring can act against the weight of the patient monitoring device pressing on the patient's chest.

At the end of the procedure, or during the procedure in the event of an emergency, the locking pin 20 can be released to pivot the ultrasound probe and the arm away from the patient. An advantage of the two-part base of the adjustable arm shown in the figures is that the ultrasound probe can be re-positioned on the patient's chest in exactly the correct position, because the joints of the arm are fixed or locked during the above-described retraction, and the arm moves as one unit.

In an embodiment of the invention not shown, the pivot axis for the tiltable portion of the base could be arranged on the other side of the multidirectional joint. By this arrangement, following a release of the tiltable portion from the fixed portion, the arm parts and the patient monitoring device could be pivoted away from the patient to the position seen in FIG. 3. In other words, by this arrangement the fixed part of the base is not formed in two parts and the two pivot axes of the base seen in the figures are in effect combined into one.

Although the example of the invention has been described in connection with ultrasound probes, the adjustable arm can also be used with other handheld medical imaging probes, such as gamma cameras for nuclear imaging, or for targeted delivery of therapy such as high-intensity focused ultrasound. 3-D ultrasound probes may be used to provide automated image-based targeting for biopsy or therapy delivery.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware comprising several distinct elements. In the device claim enumerating several means, several of these means can be embodied by one and the same item of hardware. The mere fact that certain measures are recited in mutually different dependent claims does not indicate that a combination of these measures cannot be used to advantage. Any reference signs in the claims should not be construed as limiting the scope.

The invention claimed is:

1. An adjustable arm for a patient monitoring device to be placed on a surface portion of a patient's body, said adjustable arm comprising:
   at least first and second arm parts;

a base to which the first arm part is connected, wherein the base includes mounting means for mounting the base relative to a patient support platform; and holding means for receiving the patient monitoring device, to which the second arm part is connected;

wherein the arm parts, the base and the holding means are articulated by means of joints therebetween, wherein the joints are fixable against movement while monitoring via the patient monitoring device;

wherein the joints between the first arm part and the base and between the second arm part and the holding means comprise multidirectional joints;

wherein the base has a fixed portion and a vertically tiltable portion, wherein the fixed portion comprises an upper base part connected to a lower base part, further wherein the vertically tiltable portion extends laterally to the upper base part, includes a lug that extends into a recess of the upper base part adjacent a nose portion of the upper base part, and is pivotally connected to the upper base part at the nose portion for limited pivotal movement between two positions of the vertically tiltable portion about a pivot axis of the vertically tiltable portion that extends transversely to an edge of the patient support platform, wherein the two positions include retracted and non-retracted positions representative of upper and lower positions, respectively, of the surface portion of the patient's body due to respiration, and wherein the lower base part comprises the mounting means and wherein the first arm part connects to the vertically tiltable portion, whereby, in operation, the joints are fixed against movement and the adjustable arm maintains the patient monitoring device in a desired position on the patient surface portion while allowing for movement of the patient monitoring device between upper and lower positions of the surface portion of the patient's body, via the vertically tiltable portion, due to respiration, wherein the recess of the upper base part further includes a lip that extends into the recess and the lug of the vertically tiltable portion includes a ledge, wherein the lip limits an upward movement of the vertically tiltable portion of the base, via an engagement with the ledge, as the vertically tiltable portion pivots in the upward movement.

2. The adjustable arm of claim 1, wherein the base includes resilient means which act on the lug of the vertically tiltable portion to urge the holding means either towards or away from the patient surface portion.

3. The adjustable arm of claim 2, wherein the resilient means comprises a tension or compression spring mounted on a threaded rod, wherein a spring force of the spring is adjusted by means of a nut threaded onto the threaded rod.

4. The adjustable arm of claim 1, wherein the vertically tiltable portion of the base is releasably locked in the retracted position to the fixed portion of the base by a locking pin in the upper base part located opposite the nose portion, wherein the locking pin is configured to releasably engage the lug.

5. The adjustable arm of claim 1, wherein the upper base part and the lower base part of the fixed portion of the base further comprise two parts pivotally connected together, and movable relative to one another from a closed, fixed position to an open position, thereby allowing the arm parts and the patient monitoring device to be pivoted relative to the mounting means of the base, away from the patient support platform.

6. The adjustable arm of claim 5, wherein the two parts of the fixed portion of the base are releasably locked together by a locking pin.

7. The adjustable arm of claim 1, wherein the multidirectional joints are universal joints.

8. The adjustable arm of claim 7, wherein the joint between the first and second arm parts is a pivotal connection.

9. The adjustable arm of claim 8, wherein the pivotal connection between the first and second arm parts includes a handle for simultaneously locking the pivotal connection and multidirectional joints.

10. The adjustable arm of claim 8, wherein the pivotal connection between the first and second arm parts includes an electromotor for simultaneously locking the pivotal connection and multidirectional joints.

11. The adjustable arm of claim 10, wherein the electromotor is controllable by a remote switch.

12. The adjustable arm of claim 11, wherein the remote switch is integrated in a foot pedal.

13. An assembly comprising the adjustable arm according to claim 1 and further comprising a patient monitoring device.

14. The assembly of claim 13, wherein the patient monitoring device is an ultrasound probe.

15. An adjustable arm for a patient monitoring device to be placed on a surface portion of a patient's body, said adjustable arm comprising:

at least first and second arm parts;

a base to which the first arm part is connected, wherein the base includes mounting means for mounting the base relative to a patient support platform; and holding means for receiving the patient monitoring device, to which the second arm part is connected;

wherein the arm parts, the base and the holding means are articulated by means of joints therebetween, wherein the joints are fixable against movement while monitoring via the patient monitoring device;

wherein the joints between the first arm part and the base and between the second arm part and the holding means comprise multidirectional joints;

wherein the base further comprises a fixed portion and a vertically tiltable portion, wherein the first arm part connects to the vertically tiltable portion, wherein the fixed portion comprises an upper base part connected to a lower base part, wherein the lower base part includes the mounting means, wherein the vertically tiltable portion extends laterally to the upper base part, includes a lug that extends into a recess of the upper base part adjacent a nose portion of the upper base part, and is pivotally connected to the upper base part at the nose portion for limited pivotal movement between two positions of the vertically tiltable portion about a pivot axis of the vertically tiltable portion that extends transversely to an edge of the patient support platform, wherein the two positions include retracted and non-retracted positions representative of upper and lower positions, respectively, of the surface portion of the patient's body due to respiration, wherein the base further includes resilient means which act on the lug of the vertically tiltable portion to urge the holding means either towards or away from the patient surface portion, whereby, in operation, the joints are fixed against movement and the adjustable arm maintains the patient monitoring device, received within the holding means, in a desired position on the patient surface portion while allowing for movement of the patient monitoring device between upper and lower positions of the surface portion of the patient's body, via the vertically tiltable portion, due to respiration, wherein the recess of the upper base part further includes a lip that extends into the recess and the lug of the vertically tiltable portion includes a ledge, wherein the lip limits an upward movement of the vertically tiltable portion of the base, via an engagement with the ledge, as the vertically tiltable portion pivots in the upward movement.

* * * * *